United States Patent [19]

Clark et al.

[11] Patent Number: 4,929,365

[45] Date of Patent: May 29, 1990

[54] BIOFILM CONTROL

[75] Inventors: James B. Clark; Deborah E. Langley, both of Bartlesville, Okla.

[73] Assignee: Phillips Petroleum Co., Bartlesville, Okla.

[21] Appl. No.: 408,851

[22] Filed: Sep. 18, 1989

[51] Int. Cl.$^5$ .................................................. C02F 1/76
[52] U.S. Cl. ...................................... 210/754; 210/755; 210/756; 210/758; 210/764; 435/262
[58] Field of Search ............... 210/755, 756, 758, 759, 210/760, 764; 424/661; 134/28; 435/262, 267

[56] References Cited

U.S. PATENT DOCUMENTS

| | | | |
|---|---|---|---|
| 3,082,146 | 3/1963 | Wentworth et al. | 424/661 |
| 3,164,552 | 1/1965 | Wolfson | 252/8.55 |
| 3,178,465 | 4/1965 | Huba et al. | 260/453 |
| 3,226,210 | 12/1965 | Baptist et al. | 44/66 |
| 3,585,147 | 6/1971 | Gordon | 8/108.1 |
| 4,419,248 | 12/1983 | Costerton | 210/764 |
| 4,499,077 | 2/1985 | Stockel et al. | 424/661 |

OTHER PUBLICATIONS

Annual Review of Microbiology, 43,435–64, 1987, J. W. Costerton et al., "Bacterial Biofilms in Nature and Disease".

Oil & Gas Journal, Mar. 8, 1982, pp. 253–264, I. Ruseska et al., "Biocide Testing Against Corrosion-Causing Oil-Field Bacteria Helps Control Plugging".

*Primary Examiner*—Peter Hruskoci
*Assistant Examiner*—Krisanne Shideler
*Attorney, Agent, or Firm*—Hal Brent Woodrow

[57] ABSTRACT

The present invention provides a method for the removal of biofilms composed of microorganisms from submerged surfaces in an aqueous medium comprising contacting said biofilm with an aqueous stabilized chlorine dioxide and at least one nutrient source, wherein said nutrient source is provided in an amount effective to result in the generation of one or more acidic compounds by said biofilm, and the aqueous stabilized chlorine dioxide is provided in an amount sufficient, when activated by said one or more acidic compounds generated by said microorganisms, to kill a sufficient number of microorganisms in the biofilm to result in the biofilm's removal. Optionally a second biocide may be provided with or after the nutrient source to kill any microorganisms released from the biofilm during its removal and thereby inhibit the reformation of the biofilm.

9 Claims, No Drawings

BIOFILM CONTROL

FIELD OF INVENTION

This invention relates to a method for removing biofilm from a surface submerged in water.

BACKGROUND OF THE INVENTION

Microorganisms in an aquatic environment have a marked tendency to grow on submerged surfaces, such as vessels or pipes carrying a flow of natural water. The microorganisms which colonize the surface secrete a surrounding structure called a glycocalyx which is usually composed of polysaccharides. The matrix structure formed by the microorganisms and the glycocalyx is generally referred to as a biofilm. The biofilm structure allows the microorganisms inhabiting the biofilm to remain viable during periods of environmental stress such as inadequate food, adverse temperature, drying or the presence of deleterious chemicals. In the operation of vessels or conduits carrying water such as heat exchangers, biofilms can substantially increase the resistance to fluid flow, reduce the heat transfer capacity and lead to increased corrosion of metal surfaces.

Efforts to control or eliminate biofilms have not been particularly successful. Biocides have difficulty in penetrating the glycocalyx formed by the microbes, thereby necessitating the use of a large quantity of these compounds to control biofilms. Mechanical abrasion has also been tried by passing "pigs", abrasive balls or ice crystals over the surface to dislodge biofilms. None of these methods have been particularly successful and tend to be labor intensive and expensive.

Thus it would be a significant contribution to the art to develop a simple, inexpensive, and effective process of removing biofilms from submerged surfaces.

It is thus an object of this invention to provide a simple, inexpensive, and effective process for the removal of biofilms from submerged surfaces.

Other objects, aspects, and advantages of the present invention will be apparent to those skilled in the art from the following description, examples and claims.

SUMMARY OF THE INVENTION

By the present invention there is provided a method for the removal of a biofilm compose of microorganisms from a submerged surface in an aqueous medium comprising contacting said biofilm with an aqueous stabilized chlorine dioxide, and at least one nutrient source, wherein said nutrient source is provided in an amount effective to result in the generation of one or more acidic compounds by the microorganisms in said biofilm, and the aqueous stabilized chlorine dioxide is provided in an amount sufficient, when activated by said one or more acidic compound, generated by said microorganisms to kill a sufficient number of microorganisms in the biofilm to result in the removal of said biofilm from said submerged surface.

DETAILED DESCRIPTION OF THE INVENTION

By the present invention there is provided a method for the substantial removal of biofilms formed in the presence of or the absence of light, from surfaces submerged in aqueous mediums. Recognizing additionally that the effectiveness of the present invention is also dependent upon the microorganisms which comprise the biofilm, for the purpose of this application, biofilm shall mean films composed of microorganisms which secrete at least one acid when provided with at least one nutrient source compatible with said microorganism's metabolism.

The present invention is suited for biofilms which are grown under aerobic or anaerobic conditions. These conditions are often found in the conduit means of heat exchangers but are not limited to that particular environment.

To further illustrate the practice of the present invention but in no way limiting thereof the following theoretical mechanism has been postulated. Since the biofilm is composed of a dispersion of different microorganisms embedded in a polysaccharide and water matrix, the biofilm effectively provides a protective microenvironment for the growth of microorganisms. The biofilm effectively operates to protect the microorganisms embedded in it from environmental stress including the presence of biocides in the aqueous environment surrounding the biofilm. The protection the biofilm offers is not complete, as biocides can slowly permeate the biofilm and will operate at a somewhat reduced effectiveness to kill some of the microorganisms. The aqueous stabilized chlorine dioxide used in the present invention will permeate the biofilm but remain inactive therein. To overcome the protective nature of the biofilm a nutrient solution is provided to the biofilm, which stimulates differential growth of the microorganisms in the biofilm. It is believed that the differential growth can disrupt the integrity of the biofilm and result in an enhanced suseptibility of the biofilm to biocides. Simultaneously with the growth of the microorganisms within the biofilm will also be the secretion of acidic compounds by a significant number of the microorganisms in the biofilm. These acidic compounds will activate the aqueous stabilized chlorine dioxide in the immediate vicinity of the individual microorganisms secreting the acid. The activated chlorine dioxide will then react with the microorganism thereby damaging or killing the microorganism. Due to cell death and perhaps the differential growth of the microorganisms within the biofilm, the biofilm will lose integrity and thereby be removed from the submerged surface. Providing a second biocide after the biofilm loses integrity will substantially reduce the number of microorganisms which may have survived the previous chlorine dioxide treatment and retard reformation of a biofilm on the submerged surface.

For the purpose of the present invention aqueous stabilized chlorine dioxide means compounds which contain chlorine and oxygen which in the presence of an acid generates a reactive chlorine dioxide species. Stabilized chlorine dioxides suitable for the practice of this invention are available from a variety of commercial sources including but are not limited to Bio-Cide International, Inc. (Norman, OK), under the tradenames of Oxine, Purogene, Purogene 40; International Dioxicide, Inc. (Clarke, NJ) under the tradenames of Anthium Dioxide, Anthium 200 and Carnelron; and RioLinda Chemical Co., Inc. (Sacramento, CA) tradename Dura Klor. The presently preferred aqueous stabilized chlorine dioxide is Purogene.

Preferably, the aqueous stabilized chlorine dioxide will be contacted with the biofilm before the nutrient source for a time sufficient to allow the stabilized aqueous chlorine dioxide to thoroughly diffuse into the biofilm structure. The period of time necessary for the stabilized aqueous chlorine dioxide to thoroughly diffuse into the biofilm structure will vary according to the concentration of stabilized aqueous chlorine dioxide and the nature and/or severity of the biofilm. Generally in fully formed biofilms which approximate the conditions encountered in nutrient-limited water environments, such as may be encountered in a heat exchanger, 24 hours is a sufficient time period for a dilute solution approximately 50 parts per million of aqueous stabilized chlorine dioxide to thoroughly diffuse into most biofilm structure.

The amount of aqueous stabilized chlorine dioxide and nutrient source contacted with the biofilm may also vary greatly depending upon the microorganisms which comprise the biofilm as well as the severity of the biofilm and the environment in which it was formed. The aqueous stabilized chlorine dioxide will also react with contaminating compounds within the biofilm's environment including but not limited to sulfides, $Fe^{+2}$ or $Mg^{+2}$. Therefore, the aqueous stabilized chlorine dioxide must be provided in amounts sufficient to react with contaminating compounds which may be present in the biofilm's environment and still leave enough unreacted aqueous stabilized chlorine dioxide present to react with the biofilm as it generates acidic compounds to kill a sufficient number of the microorganisms in the biofilm to result in the removal of the biofilm.

Those of skill in the art will recognize that the amount of aqueous stabilized chlorine dioxide sufficient to result in the removal of the biofilm will thus vary depending upon the environment in which it is being used. By way of guidance but no way as a limitation on the present invention it has found that as little as 50 parts per million aqueous stabilized chloride dioxide in a DATS (Deposit Accumulation Testing System) under aerobic conditions with a hundred parts per million glucose is effective to return the system back to near clean pipe values within 24 hours.

The nutrient source used in the present invention may consist of any mixture of nutrients which are compatible with the metabolism of the microorganisms in the biofilm and which respond to said nutrient source by secreting at least one acidic compound. Those skilled in the art will recognize that a variety of nutrient sources may be used depending upon the microorganisms which comprise the biofilm which would result in the secretion of at least one acidic compound. Suitable non-limiting examples of readily available nutrient sources which would be expected to work on a broad range of biofilms include but are not limited to glucose and crude cane molasses. The nutrient source should be provided in amounts effective to stimulate the secretion of acidic compounds within the biofilm.

Optionally, a second biocide or blends of biocides may be contacted with the biofilm simultaneously with, or after the contacting of the nutrient source with the biofilm. The second biocide may be utilized to prevent the survival of any microbes resistant to the aqueous stabilized chlorine dioxide-nutrient source treatment of the biofilm. Preferably the aqueous stabilized chlorine dioxide will be contacted with the biofilm followed by contacting the nutrient media with the biofilm and then contacting the second biocide or blends thereof with the biofilm or aqueous remnants thereof. The second biocide or blends of biocides should be provided in amounts effective to kill remaining microorganisms from the biofilm which may exist in the biofilm, as aqueous remnants of the biofilm, or as planktonic cells.

Biocides known to those skilled in the art suitable for control of biofilms may be utilized for this purpose. Biocides may be selected from several classes of biocides including but not limited to biocides selected from the group consisting of amine-based biocides, aldehyde-based biocides, organohalide-based biocides, oxidative biocides, heavy metal-based biocides, sulfur based biocides, and blends thereof. Suitable amine-based biocides include but are not limited to amine-based biocides selected from the group consisting of monoquaternary, diquaternary, and low molecular weight salts of fatty amines (such as tallow diamine and cocco diamine). Suitable aldehyde-based biocides include but are not limited to aldehyde-based biocides selected from the group consisting of monoaldehydes (such as formaldehyde and acrolein), dialdehydes (such as glutaraldehyde), and formaldehyde-releasing compounds (such as triazines). Suitable organohalide-based biocides include but are not limited to chlorinated phenols (such as tri-chloro-phenols and penta-chloro-phenols), and brominated compounds (such as dibrimo-nitrilo-propionamide). Oxidative biocides include but are not limited to oxidative biocides selected from the group consisting of chlorine, sodium hypochlorite, and oxygen-based biocides (such as ozone). Suitable heavy metal-based biocides include but are not limited to heavy metal-based biocides selected from the group consisting of tributyltinoxide and copper sulfate. Suitable sulfur-based biocides include but are not limited to sulfur-based biocides selected from the group consisting of methylene-bis-thiocyanate, isothiazolins, sodium alkyl thiocarbamates, potassium alkyl thiocarbamates, and metronidazole. Suitable blends of these biocides include but are not limited to blends selected from the group consisting of quaternary amines and aldehydes, quaternary amines and heavy metals, and blends of different types of thiocarbonates and blends of different types of isothiazolins. The preferred second biocide to be contacted with the aqueous medium as the biofilm is being removed is gluteraldehyde.

The following nonlimiting examples are provided to illustrate the practice of the present invention.

EXAMPLE I

Biofilms were modeled utilizing a Deposit Accumulation Test System (DATS) manufactured by Bridger Scientific of Sandwich, Massachusetts. The DAT System continuously monitors the changes in heat transfer resistance (HTR) and friction reduction factor (FRF) for a set length of stainless steel tubing connected to a continuous recirculating system. The continuous recirculating system utilizes water similar to that which would be found in a typical conduit. Water was fed into the system at a rate to give a complete replacement of the system volume each 24 hours. All nutrients or other additives were introduced into the system to maintain a constant concentration throughout each 24 hour period.

Prior to the beginning of each experiment the DAT System was cleaned and the HTR and FRF values were determined. The beginning values after cleaning the DAT System were by convention called the "clean tube values". The continuously recirculating water utilized in the following experiments was obtained from the Arkansas-Burbank system. (Arkansas-Burbank water system is a fresh water system used in the Burbank oil field, Osage County, OK). The water obtained from the Arkansas-Burbank system was untreated fresh water. The DAT System was first purged with air and then nitrogen. Difco nutrient broth media was then continuously added to maintain a concentration of 200 parts per million in the recirculating Arkansas-Burbank System water. The formation of the biofilm was monitored by taking HTR and FRF readings every 20 seconds. The biofilm formation was also evaluated optically using a Robbins stud (see McCoy, W. F., Bryer, S. J. D., Robbins, J., and Costerton, J. W. 1981. "Observations of Fouling Biofilm Formation" *Can. J. Microbiol.* 27:910–917".) When the HTR and FRF became relatively constant (which occurred approximately after 1000 hours of recirculation) the biofilm formation was presumed to be stabilized. At this point the biofilm was also observed via the Robbins stud to verify the formation of a complete biofilm. After this point experimentation on the biofilm could begin.

EXAMPLE II

A biofilm was produced in accordance with Example I. During the experiment the biofilm was fed with Nutrient broth to give a continuous concentration of 200 ppm. The biofilm was subjected to the tests given in Table I, which lists the hours of the experiment, HTR, FRF, and the various treatments performed on the biofilm.

TABLE I

| Time in Hours | HTR Heat Transfer Resistance $M^2 \cdot °C./Watt$ | FRF Friction Reduction Factor | Treatment* | |
|---|---|---|---|---|
| | | | Purogene | Dextrose |
| 0 | 0.46 | 26.5 | 0 ppm | 0 ppm |
| 1361 | 0.64 | 42.0 | 50 ppm | 100 ppm |
| 1514 | 0.75 | 58.0 | 50 ppm | 0 ppm |
| 1653 | 0.64 | 59.0 | 50 ppm | 100 ppm |
| 1823 | 0.47 | 60.0 | 0 ppm | 0 ppm |
| 2348 | 0.80 | 93.0 | 0 ppm | 100 ppm |
| 2495 | 0.68 | 35.0 | 50 ppm | |

*Amounts given are the concentration in parts per million.

After 1361 hours of formation, the biofilm had attained a degree of stability as measured by both HTR and FRF. At this time, Purogene was added to give a continuous concentration of 50 ppm and dextrose to give 100 ppm. By 1514 hours, both HTR and FRF continued to increase slightly, and the dextrose feed was stopped. With the Purogene alone, there was a slight drop in HTR, but no change in FRF. Dextrose was restarted at 100 ppm at 1653 hours, and HTR returned to near clean tube value, although FRF remained elevated. Microscopic examination revealed a remaining rough surface on the metal surface. At 1823 hours, both Purogene and dextrose feeds were stopped. Both HTR and FRF increased until, at 2348 hours, 100 ppm dextrose was added. By 2495 hours, HTR and FRF both decreased, showing the effect of the dextrose alone. When 50 ppm Purogene was added at 2495 hours, there was a slight decrease in HTR.

This example demonstrates that the use of Purogene alone, or dextrose alone, has less effect in reducing the biofilm than the addition of Purogene followed by dextrose. Purogene and dextrose added at the same time has less effect than the sequential use of these materials. These results indicate that, with adequate time, the Purogene penetrates the biofilm but remains relatively inactive until the dextrose is added. The microbial production of organic acids from metabolism of the dextrose activates the Purogene at the site of the acid-producing cell and kills the cell.

EXAMPLE III

A biofilm produced in accordance with the procedures in Example I was subjected to the following tests. This was a test run in parallel with Example II on a second DATS unit.

TABLE II

| Time in Hours | HTR Heat Transfer Resistance $M^2 \cdot °C./Watt$ | FRF Friction Reduction Factor | Treatment* | |
|---|---|---|---|---|
| | | | Purogene | Dextrose |
| 0 | 0.21 | 25.3 | 0 ppm | 0 ppm |
| 1361 | 1.26 | 380 | 50 ppm | 0 ppm |
| 1514 | 1.52 | 370 | 50 ppm | 100 ppm |
| 1680 | 0.31 | 30 | 50 ppm | 200 ppm |
| 1727 | 0.36 | 30 | 50 ppm | 0 ppm |
| 1823 | 0.35 | 30 | 0 ppm | 0 ppm |

*Amounts given are the concentrations in parts per million.

At 1361 hours the biofilm showed relative stability in that both HTR and FRF were increasing very slowly. At this time the addition of 50 ppm Purogene to the system showed no effect on HTR and caused a slight reduction in FRF by 1514 hours. At 1514 hours, 100 ppm dextrose was added to the system in addition to the Purogene treatment. By 1680 hours both HTR and FRF had dropped to nearly clean tube values. At 1680 hours the dextrose concentration was increased to 200 ppm, and by 1727 hours the additional dextrose had little effect. At 1727 hours the dextrose was discontinued while 50 ppm Purogene was continuously administered. Both HTR and FRF values remained essentially constant until the experiment was terminated at 1823 hours.

This example demonstrates that the preferred process of administering an aqueous stabilized chlorine dioxide followed by the addition of a nutrient source to a conduit system will result in removal of biofilm to the extent that both HTR and FRF are returned to near clean tube values. This example also demonstrates that the biofilm will not quickly rebuild after treatment with the present invention.

That which is claimed is:

1. A method for the removal of biofilms composed of microorganisms from a submerged surface in an aqueous medium comprising contacting said biofilm with
   (i) an aqueous stabilized chlorine dioxide; followed by;
   (ii) at least one nutrient source; wherein said nutrient source is provided in an effective amount to result in the microorganisms in the biofilm generating one or more acidic compounds and said aqueous stabilized chlorine dioxide is provided in an amount sufficient, when activated, by said one or more acidic compounds generated by said microorganisms to kill a sufficient number of the microorganisms in the biofilm to result in the removal of said biofilm from said submerged surface.

2. The method of claim 1 wherein a second biocide is added after said aqueous stabilized chlorine dioxide in an effective amount to be toxic to microorganisms which may be released upon removal of the biofilm.

3. The method of claim 2 wherein said second biocide is selected from the group consisting of amine-based biocides, aldehyde-based biocides, organohalide based biocides, oxidative biocides, heavy metal-based biocides, sulfur-based biocides, and blends thereof.

4. The method of claim 3 wherein said biocide is an amine-based biocide selected from the group consisting of monoquaternary amines, diquaternary amines, and a low molecular weight salt of a fatty amine.

5. The method of claim 3 wherein said biocide is an aldehyde-based biocide selected from the group consisting of monoaldehydes, dialdehydes, and formaldehyde-releasing compounds.

6. The method of claim 3 wherein said biocide is an organohalide-based biocide selected from the group consisting of chlorinated phenols and dibromo-nitrilopropionamide.

7. The method of claim 3 wherein said biocide is an oxidative biocide selected from the group consisting of chlorine, sodium hypochlorite, and oxygen-based biocides.

8. The method of claim 3 wherein said biocide is a heavy metal-based biocide selected from the group consisting of tributyltinoxide and copper sulfate.

9. The method of claim 3 wherein said biocide is a sulfur-based biocide selected from the group consisting of methylene-bis-thiocyanate, isothiazolins, sodium alkyl thiocarbamates, potassium alkyl thiocarbamates, and metronidazole.

* * * * *